United States Patent [19]

Gray et al.

[11] Patent Number: 5,436,979
[45] Date of Patent: Jul. 25, 1995

[54] PROCESS FOR DETECTING AND MAPPING DIRT ON THE SURFACE OF A PHOTOGRAPHIC ELEMENT

[75] Inventors: Robert T. Gray, Rochester; David L. Patton, Webster, both of N.Y.

[73] Assignee: Eastman Kodak Company, Rochester, N.Y.

[21] Appl. No.: 934,089

[22] Filed: Aug. 21, 1992

[51] Int. Cl.$^6$ .......................................... G01N 21/88
[52] U.S. Cl. ................................. 382/141; 348/92; 382/2.54; 356/443
[58] Field of Search ................. 382/8, 54; 358/106; 377/10, 11; 356/389, 443, 394, 237; 348/128, 130, 92

[56] References Cited

U.S. PATENT DOCUMENTS

| | | | |
|---|---|---|---|
| 3,988,602 | 10/1976 | Gorsica, Jr. | 382/41 |
| 4,189,235 | 2/1980 | Guter et al. | 356/239 |
| 4,365,895 | 12/1982 | Shaber et al. | 356/444 |
| 4,669,885 | 6/1987 | Ina | 356/443 |
| 4,677,680 | 6/1987 | Harima et al. | 382/1 |
| 4,698,843 | 10/1987 | Burt et al. | 382/54 |
| 4,868,773 | 9/1989 | Cayle et al. | 364/724.01 |
| 4,907,156 | 3/1990 | Doi et al. | 382/6 |
| 4,958,307 | 9/1990 | Nishimura | 364/55.01 |
| 4,975,768 | 12/1990 | Takaraga | 358/75 |
| 4,977,521 | 12/1990 | Kaplan | 364/525 |
| 5,033,095 | 7/1991 | Marcantonio | 382/8 |
| 5,036,405 | 7/1991 | Kojima | 358/448 |
| 5,065,257 | 11/1991 | Yamada | 358/463 |
| 5,091,963 | 2/1992 | Litt et al. | 382/8 |
| 5,179,419 | 1/1993 | Palmquist et al. | 382/8 |

FOREIGN PATENT DOCUMENTS

| | | | |
|---|---|---|---|
| 3215067 | 10/1983 | Germany | G01N 21/89 |
| 62-224868 | 10/1987 | Japan | G06F 15/66 |
| 2127647 | 4/1984 | United Kingdom | H04N 1/40 |
| WO91/18281 | 11/1991 | WIPO | G01N 21/88 |

OTHER PUBLICATIONS

Hitachi Review, vol. 40, No. 6, Dec., 1991, pp. 395–400, by T. Nishino et al, "Reticle Particle Detection System".

Pattern Recognition Letters, vol. 2, No. 2, Dec., 1983, pp. 89–93, IP et al, "Impulse Noise Cleaning By Interative Threshold Media Filtering".

Systems And Computers In Japan, vol. 18, No. 2, 1987, Meada et al, "A Restoration Scheme For Images With Missing Parts".

*Primary Examiner*—Joseph Mancuso
*Assistant Examiner*—Larry J. Prikockis
*Attorney, Agent, or Firm*—Edward Dugas

[57] ABSTRACT

A method and associated apparatus for detecting the amount, size, shape, and location of anomalies, such as dirt and scratches, on the surface of a test photographic element after the application of a cleaning procedure and for objectively determining the effectiveness of the film cleaning devices and procedures at removing dirt from photographic negatives and slides and the scanner's sensitivity to the artifacts on the test photographic element's surface. The test photographic element is scanned and the scanned image is digitized and converted to color digital count values. The count values are corrected for systematic errors and a set of context dependent threshold values on the corrected data is computed. If the corrected data passes any of the series of threshold tests it classified as anomalous otherwise it is considered to be background or clean. A series of statistics are calculated for the detected anomalies and are reported to the operator. This report enables the operator to monitor and maintain the quality of the cleaning process.

12 Claims, 2 Drawing Sheets

PROCESS FOR DETECTING AND MAPPING DIRT ON THE SURFACE OF A PHOTOGRAPHIC ELEMENT

TECHNICAL FIELD OF THE INVENTION

The present invention is related to the field of determining the amount, size, shape, and location of dirt and scratches on the surface of a photographic element.

A portion of the disclosure of this patent document contains material which is subject to copyright protection. The copyright owner has no objection to the facsimile reproduction by any one of the patent disclosure, as it appears in the Patent and Trademark Office patent files or records, but otherwise reserves all copyright rights whatsoever.

BACKGROUND OF THE INVENTION

Known methods and apparatus for determining the amount of dirt or the number of scratches on a photographic element's surface such as a negative or slide require either a visual inspection of the negative or slide and manual recording of the data or the making of a photographic print followed by the visual inspection of the print and the manual recording of the data. This procedure is very labor intensive and time consuming in the first case, and very labor intensive, time consuming, and wastes paper in the second case.

A patent of interest for its teaching in this art is U.S. Pat. No. 4,189,235, entitled "Test Device For Dynamically Measuring The Degree of Dirt Accumulation On Bank-Notes" by Guter et al. This patent describes a method for inspecting opaque web materials for dirt accumulation. The reflected signal from a light source is sensed by three adjacent photosensors which scan the material. When the signal from the center sensor is significantly different then the side sensors the local region is classified as dirt. Materials with greater than a predetermined rate of detected dirt regions are rejected. Potential problems with this invention include sensitivity to noise in the reflected signal due to either normal variations or system noise which makes it difficult to set robust thresholds on the difference signals and the restriction to sensing in a linear array of three sensors.

In digital scanning systems it is not possible for the scanner to distinguish between the real photographic image and surface artifacts such as dirt and scratches. Therefore, the artifact is scanned and digitized as part of the photographic image. When the scanned image is written to memory or written as hard copy, the artifact, which was not part of the photographic image, is also written along with the photographic image itself. In conventional optical printing systems, if dirt or a scratch appears on the photographic image, the photographic negative or slide may be cleaned and the print remade or the print itself maybe retouched. In the case where the images are written to an optical disc, it is not convenient nor desirable to rewrite the image, because many images are written onto a disc before the images are viewed, and once an image is written it cannot be removed. Therefore it is necessary to monitor the dirt present in the photofinishing environment and to assess the effectiveness of film cleaning methods.

Another patent of interest is U.S. Pat. No. 4,677,680, entitled "Method And Device For Inspecting Image" by Harima et al. In this patent a method is described for inspecting a moving web media for defects. The density values of local regions in the imaged medium are compared with a predetermined true image of that region. Differences between the true and imaged signals are compared to a threshold. This method has the potential problems of requiring an integral registration step between the true and sensed images in addition to adding complexity this step does not compensate for differences in spatial illumination variations across the medium or random noise differences.

Yet another patent of interest is U.S. Pat. No. 5,033,095, entitled "Scanning Image Analyzer For Accumulating Quantifiable Contaminants of Webs" by J. J. Marcantonio. This patent teaches a system for inspecting test sheets of web material e.g. paper and reporting the results to an operator via a display. The pixel brightness values of a scanned image are thresholded to create a pixel map of detected dust. contiguous dust regions on this map are calculated and a report of the number and size of the dust regions is displayed to the operator. The key difficulty with such a system is again the determination of suitable signal thresholds to provide robust detection in the presence of spatial variations in illumination and of system noise. In the application of the system to the scanning of film transparencies a fair amount of the contaminating dirt is partially transparent and generates only a slight signal difference from that of the uncontaminated medium. The system also places constraints on the quality of both the test target and the scanner with regard to minimizing spatial variations in brightness, because of the use of a single threshold across the image.

The present invention solves the aforementioned problems with an apparatus and a method for determining the amount, size, shape, and location of the artifact. In particular, the invention describes a robust method for setting a spatially continuous series of thresholds across the image which are insensitive to spatial brightness variations in the test target or the scanner illumination and sensor and which allows the detection of contaminants whose brightness signal overlaps the local brightness distribution of the background medium. The present invention is extremely operator friendly in that in that normal operation requires no user adjustments of the parameters. The present invention also allows for unique adjustment of the detected dust region map to compensate for marginal coverage of sensor areas by dirt fragments and visually insignificant breakages of large dirt fragments.

SUMMARY OF THE INVENTION

In one embodiment of the invention there is provided the steps of:
(a) forming image data of a sample of the medium;
(b) storing the formed image data produced from step (a);
(c) conditioning the stored image data to remove spatial variations not caused by anomalies; and
(d) comparing the stored image data with a set of reference conditions to determine the existence of an anomaly.

In a preferred embodiment of the invention the stored digital image is mapped to units linearly proportional to photographic density or log-exposure and a digital residuals image is created which is a per-pixel map of the original-resolution image less a spatially smoothed version of the image. From the residuals image the frequency of occurrence (or histogram) of levels in the digital residuals map for the non-anomalous pixels is determined. A set of brightness thresholds is calculated for the digital residuals image from the residual histogram which will comprise appropriate thresholds for detection of a set of possible events within a local region in the residuals image. A local region (window) in the image is digitally extracted about each sample in the image which is then tested against the appropriate threshold according to the state of the window contents. A decision is made on the basis of whether the center sample in the window, at each window location, will be classified as one of several possible sample classes. A map of sample classes is created, and segmented into uniquely labeled segments containing all spatially contiguous samples of a single sample class. A report of the sets of attributes for the segments is then formed.

It is a primary object of the present invention to provide an apparatus and associated method for automatically and accurately mapping the amount, size, shape, and location of anomalies on the surface of a photographic element.

It is another object of the present invention to objectively measure the effectiveness of how well film cleaning devices and procedures remove dirt from a photographic element's surface and to determine a scanner's sensitivity to dirt on the photographic element's surface.

These and other objects of the present invention will become more apparent when taken in conjunction with the following description and drawings wherein like characters indicate like parts and which drawings form a part of the present description.

DESCRIPTION OF THE PREFERRED EMBODIMENTS

Figure 1:
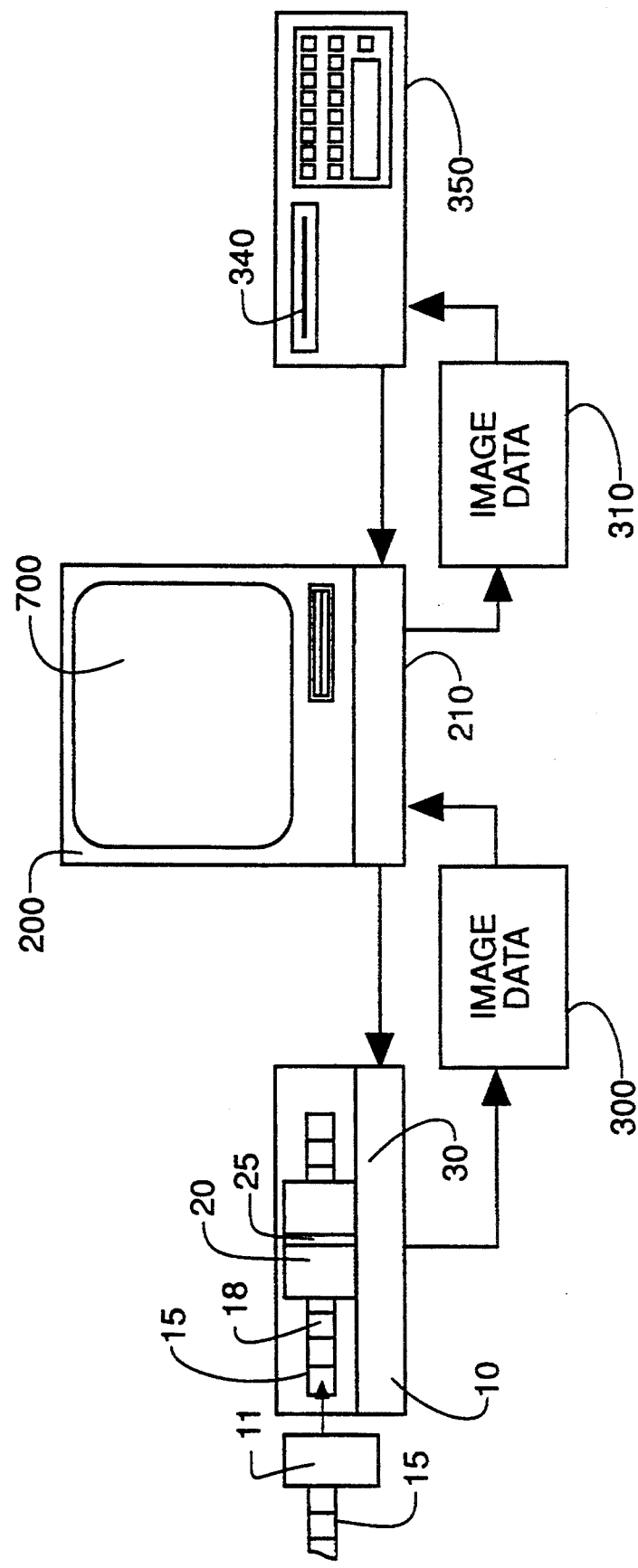
FIG. 1 is a block diagram of the digitizing scanner, control logic and memory, and the optical disc writer.

Referring to FIG. 1, the present invention is implemented using a digitizing scanner 10, a control and logic device 200, such as a computer with a display device 700, and an optical disc writer 350. As shown, a test photographic element(s) 15 such as a strip of film, containing one or more frames 18 which have been exposed to a uniform density that is slightly above the fog level of the film, is passed through a film cleaner 11 and is placed into a scan gate 20 where the test photographic element(s) 15 is driven past a scan head 25, under control of the scanner's control and logic circuitry 30. It is noted that the film grain of the photographic element 15 has an essentially Gaussian density distribution. As each frame 18 is scanned the resultant scanned image data, represented by block 300, is digitized and transmitted to a memory 210 for storage. The computer 200 process the stored data, in a manner to be described, to provide output image data 310 which may be written to an optical disc 340 by the optical disc writer 350 to provide a report as to the characteristics of the anomalies. The scanning device 10 is capable of quantizing pixel values into multiple brightness levels in separate red, green, and blue channels. A minimum number of brightness levels is 64 and a typical number is 256. The stored image data 300 is classified and mapped by an image classifier 250 as the flow chart shown in FIG. 2 and described below.

A determination of how well a film cleaning process is performing can be easily achieved with the present process by recording the image data (anomalies) from an uncleaned piece of film and then cleaning the film and rescanning the film to generate a second set of recorded data that is then compared against the first recorded image data. A commercially available film cleaner sells under Kodak's catalog No. 128 1724 and is manufactured by Print Masters Products 18740 Oxnard St #315 Tarzana, Calif. 91356.

Figure 2:
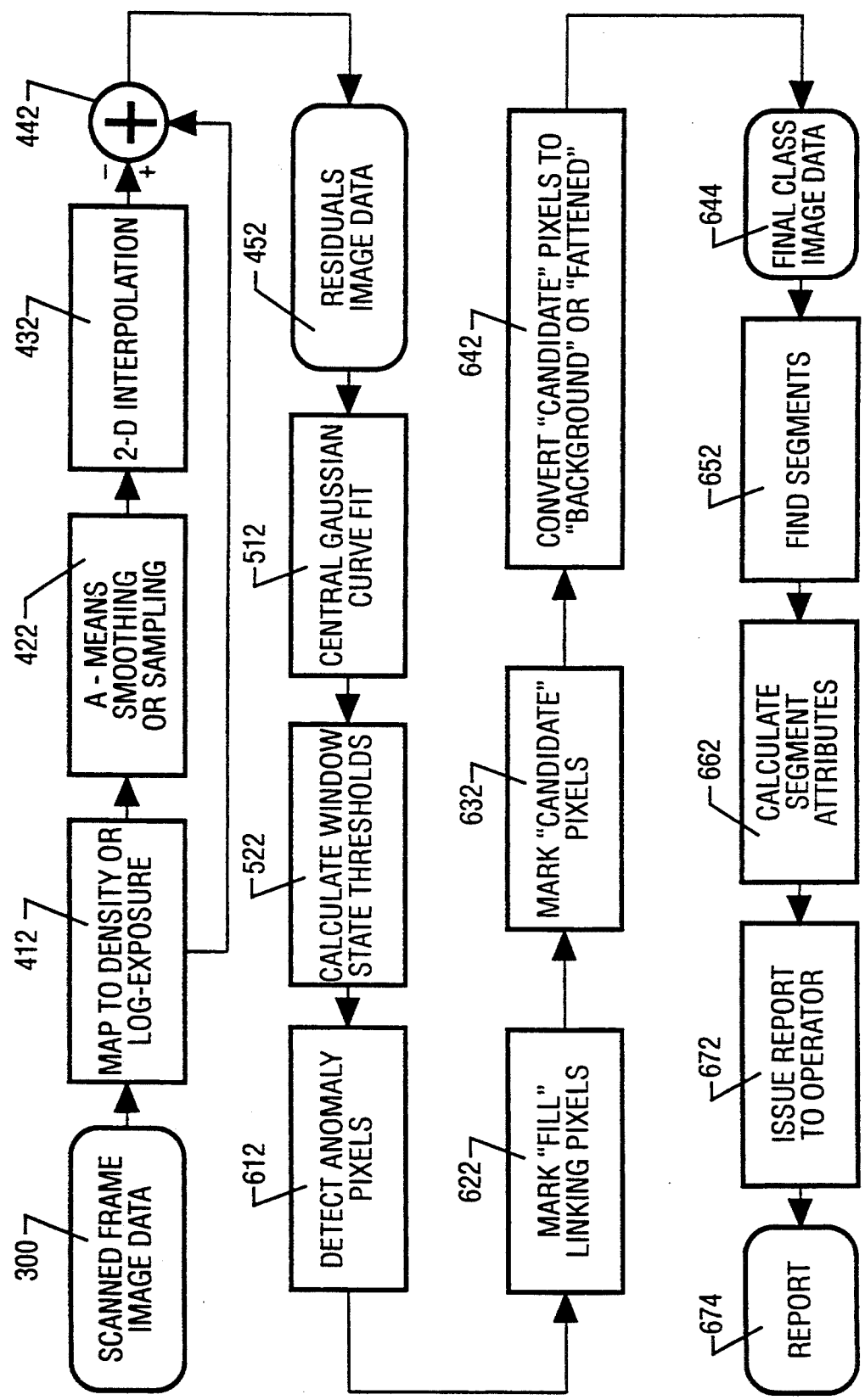
FIG. 2 is a block flow chart illustrating a detection and classification process.

In FIG. 2 there is illustrated a preferred embodiment of the present invention which provides information as to the characteristics of the anomalies. The pixel values, for the scanned frame image data 300, for one or more of scanned spectral bands, are converted to values which are linearly proportional to either optical log-exposure or to optical density in block 412. The preferred method selects one of the three scanned color bands based on the maximum density difference between the mode (most common) density and the maximum density of the scanned test element (which will be dominated by anomalous samples).

The digital image of samples which are so mapped are then spatially averaged in block 422 using an alpha-trimmed means operation to estimate the local value of the "background" (i.e. non-"anomalous") samples. The alpha-trimmed mean operation effectively filters the Gaussian characteristics of the original input image. As the mapped brightness values of the anomalous samples predominantly occurs in the extreme small transmission values of the scanned image, the alpha-trimmed mean operation is resistant to the anomalous values. Thus, the alpha-trimmed mean filter effectively filters the Gaussian additive noise which characterizes the film grain density values, yet is insensitive to the presence or absence of the relatively bright outliers in the image data, which may result from the dust fragments and other anomalies targeted by the present invention. Processing is performed on contiguous but non-overlapping rectangular blocks of the image to minimize computation. The alpha trimmed-mean's values are then spatially interpolated by cubic convolution back to the original spatial dimensions of the digital image. This is accomplished by taking the difference between the output of the 2-D interpolation block 432 and the output from the alpha means smoothing and sampling block 422. The resulting map of alpha-smoothed brightness values is then digitally subtracted from the map of non-smoothed brightness values in block 442. This produces a "residuals" map of image data, 452, that is relatively free from any gradual exposure variations across the image that were present in the scanned digital image of the test element. Such being the case it is used to perform the rest of the anomaly detection process on the image. The smoothed image created by the alpha-trimmed mean operation effectively filters the Gaussian characteristics of the original input image and is also resistant to the anomalies. Thus, the resultant residual image will retain the Gaussian characteristics of the film grain density distribution of the original input image, as well the anomalies, if any. Accordingly, anything in the residual image that is sufficiently different from the Gaussian probability distribution model can be presumed to be an anomaly.

The present method makes use of a sliding rectangular detection window operation on the residuals image. The window, for example, may be a 5×5 matrix of samples. At each window location the samples within the window are tested against a series of threshold criteria; if the window contents pass any of the tests, then a class value of "anomalous" is set for the center of that window location; if the window contents at a location fail all of the tests a class value of "background" is set for that location. The threshold tests evaluate whether n or more samples (one of which is the center sample) within the window have residual levels equal to or greater than a threshold level above the residuals mean level value (equal to zero). The threshold levels for the various n values to be used in the test sequence are automatically calculated prior to the detection windowing operation in block 522. They are based upon insuring a desired maximum false alarm rate at a specified statistical confidence, for each threshold test (i.e. for each n value). The maximum allowable number of false alarms per test is preset within the algorithm to zero per image per n level. The confidence level is adjustable and is nominally set at 0.95. The higher the setting of the confidence level, the less sensitive is the algorithm to the presence of dirt. In the preferred implementation, this confidence level is based upon automatically fitting a Gaussian curve to the central (near-zero) values of the histogram of residuals brightness levels in block 512. For photographic film which has been scaled to proportional density units as in block 412 this is a good assumption.

The resulting set of class values, for each image sample, forms and maps an image which may optionally be refined to correct for additional characteristics in the image data.

The preferred implementation allows options for two such occurrences. In the first case of block 622, small natural breakages on the order of one sample in size may occur in the class map between "anomalous" samples, due to actual breakages of extended dust fragments. A human observer of a class map (and the original image) would readily identify the separate pieces of "anomaly" so created as effectively a single fragment. When the purpose of the analysis processing is to analyze dust, the properties of the ambient dust prior to any stress-induced breakage, or to provide a correlation between features and subjective image quality, then the "fill" option is selected by the operator. Under this option, all "background" -class samples which form single-pixel gaps between "anomalous" -class samples are reclassified as a special "fill" class. This is implemented by comparing every 3×3-sample neighborhood in the class map with a set of eight 3×3-sample templates; a match to any of the templates causes the center "background" class value to be changed to a special "fill" class value. During subsequent segmentation, this class may optionally be treated as an "anomalous" class value.

The second optional processing on the class map is intended when accurate measurement of individual anomaly fragments is important. In normal operation, as previously described, the widths of dust fragments may be slightly underestimated due to, e.g., only partial coverage of scanner samples by dust or scratches. The operator may compensate for this by use of the "fatten" option of block 642. Processing for this option occurs in two steps; In block 632 all "background' samples in the post-detection class map which have an "anomalous" sample as a nearest neighbor and which have a residual brightness value within a specified range of the closest threshold level used in the detection processor are labeled as "candidate"samples. In the second step, executed in block 642, local 3×3-sample neighborhoods about each candidate sample are examined. If the candidate sample is a non-connecting extension from other non-background samples ("anomalous", "fill", or "candidate") then it remains classified as "background"; otherwise its class is relabeled as "fattened". The resulting dilation of the original class fragments thus is no greater than one sample in distance from a true "anomalous" sample. As for the "fill" option, the resulting "fattened" sample is optionally treated as "anomalous" in the subsequent segmentation processing.

The segmentation step 652 connects spatially contiguous (eight-connected) class samples of the same effective "non-background" class and assigns a unique index value to the resulting segment. Attributes or features describing shape, contrast, and location are then computed for each segment 662. These features preferable consist of the segment area, average brightness of the original scanned levels in the segment, image location of the centroid of the segment, distance of the centroid from the image center, and shape parameters (eccentricity and size of bounding rectangle). An output report 674 to the operator is then generated in block 672 as a text file containing these features which are reported as statistics (mean, standard deviation, minimum and maximum) for each segment area, as well as single-segment features for the largest-area anomaly segments in the image.

Appendix A is a source code listing of a program that accomplishes the present invention when run on a VAX computer operating with a VAX FORTRAN compiler and the VMS operating system.

While there has been shown what are considered to be the preferred embodiments of the invention, it will be manifest that many changes and modifications may be made therein without departing from the essential spirit of the invention. It is intended, therefore, in the annexed claims, to cover all such changes and modifications as may fall within the true scope of the invention.

We claim:

1. A method for determining the presence of anomalies on the surface of a photographic element having a film grain, said film grain having an essentially Gaussian density distribution, said method comprising the steps of:

(a) forming non-enhanced original image data of a sample of the photographic element;

(b) storing the formed non-enhanced original image data produced from step (a);

(c) forming an alpha-trimmed mean smoothed rendition of the non-enhanced original image data, said alpha-trimmed mean smoothed rendition of the non-enhanced original image data effectively filtering said essentially Gaussian density distribution of said film grain and being resistant to the presence of said anomalies;

(d) conditioning the stored non-enhanced original image data to remove spatial variations not caused by anomalies by calculating the difference image between the non-enhanced original image data and the alpha-trimmed mean smoothed rendition of the non-enhanced original image data to form conditioned original image data values, said conditioned original image data values retaining said essentially Gaussian density distribution of said film grain; and (e) comparing the formed conditioned original image data values with a plurality of reference conditions based on Gaussian probability statistics of said film grain to determine the existence of an anomaly.

2. The method according to claim 1 and further comprising the step of:
(f) determining the number of anomalies of step (e).

3. The method according to claim 2 and further comprising the step of:
(g) determining the size of the anomalies.

4. The method according to claim 2 or 3 and further comprising the step of:
(h) creating a map of the positions of the anomalies on the surface of the photographic element.

5. A method for determining the amount, size, shape and location of anomalies on the surface of a test photographic element such as a negative or positive transparency; comprising the steps of:
(a) passing a test photographic element through a digitizing scanner and scanning the test photographic element and any anomaly such as dirt located on the surface of the test photographic element to provide digitized image data;
(b) storing the digitized image data in units proportional to optical density of the test photographic element;
(c) respecifying the stored digitized image data to identify anomalies by:
  i. removing spatial variations in the digitized image data caused by other than anomalies or noise by means of creating a difference image between said digitized image data and an alpha-trimmed mean smoothed version of said digitized image data to form corrected digital image values;
  ii. determining a residuals distribution model for the corrected digital image values for step (i);
  iii. determining a set of condition thresholds for a plurality of spatial contexts about a number of corrected digital image values to ensure a desired tolerable false alarm rate;
  iv. classifying each corrected image data value into an anomaly data value or a background data value as a function of said determined set of condition thresholds;
(d) reclassifying to anomaly data values those background data values that are spatially near anomaly data values and whose corresponding corrected data values are less than but near to one or more of said determined set condition thresholds;
(e) creating a list of the amount, size, location and shape of the identified anomalies of step (c) and (d) by:
  v. segmenting the map of anomaly data values into contiguous spatial regions;
  vi. calculating for each of said spatial regions at least one of the following values: area, centroid location of the anomaly, bounding spatial coordinates, eccentricity, and average digitized image data value; and
  viii. outputting a list of the calculated values from step (e) vi.

6. A method having particular utility in the determination of the quality of a cleaning process applied to a photographic element having a film grain, said film grain having an essentially Gaussian density distribution, said method comprising the steps of:
(a) scanning the photographic element to produce data representing surface anomalies;
(b) storing the data produced from step (a);
(c) comparing the stored data with a set of reference conditions to determine the existence of an anomaly, said reference conditions being determined by fitting a Gaussian probability distribution model to said stored data and determining a plurality of thresholds which provide a desired tolerable number of background image data values being labelled as anomalies based upon the spatial context of a local region about each stored data value;
(d) determining the number of anomalies in existence;
(e) determining the size and shape of the anomalies;
(f) creating a map of the positions of the surface anomalies on the photographic element;
(g) cleaning the photographic element with the cleaning process; and
(h) repeating steps (a) through (f) and comparing the created maps to determine the differences therein as a function of the quality of the cleaning process.

7. A method for detecting and classifying anomalies on a photographic element having a film grain, said film grain having an essentially Gaussian density distribution, said method comprising the steps of:
(a) scanning the photographic element to form digitized pixel values;
(b) converting the digitized pixel values to linearly proportional optical log-exposure values;
(c) spatially calculating alpha-trimmed means of the optical log-exposure values to provide averaged optical log-exposure values, said averaged optical log-exposure values effectively filtering said essentially Gaussian density distribution of said film grain and being resistant to the presence of said anomalies;
(d) forming the difference between the optical log-exposure values of step (b) and the averaged optical log-exposure values of step (c) to produce a map of residuals values, said residuals values retaining said essentially Gaussian density distribution of said film grain; and
(e) forming neighborhood groups of residuals values which are compared to a plurality of threshold criteria based on Gaussian probability statistics of said film grain for classifying the residual values of a neighborhood group as an anomaly if the threshold criteria is met.

8. Apparatus for detecting and classifying anomalies on a photographic element having a film grain, said film grain having an essentially Gaussian density distribution, said apparatus comprising:
(a) means for scanning the photographic element to form digitized pixel values;
(b) means for converting the digitized pixel values to linearly proportional optical log-exposure values;
(c) means for spatially calculating alpha-trimmed means of the optical log-exposure values to provide averaged optical log-exposure values, said averaged optical log-exposure values effectively filtering said essentially Gaussian density distribution of said film grain and being resistant to the presence of said anomalies;
(d) means for forming the difference between the optical log-exposure values from said means for converting the averaged optical log-exposure values from said means for spatially averaging to produce a map of residuals values, said residuals values retaining said essentially Gaussian density distribution of said film grain; and
(e) means for forming neighborhood groups of residuals values which are compared to a plurality of threshold criteria based on Gaussian probability statistics of said film grain for classifying the residual values of a neighborhood group as an anomaly if the threshold criteria is met.

9. Apparatus for determining the amount, size, shape and location of anomalies on the surface of a test photographic element such as a negative or positive transparency; comprising:

means for scanning a test photographic element and any anomaly such as dirt located on the surface of the test photographic element to provide digitized image data;

means for storing the digitized image data in units proportional to optical density;

means for re-specifying the digitized image data stored in units proportional to optical density to identify anomalies by:

i. removing spatial variations in the digitized image data caused by other than anomalies or noise by means of creating a difference image between said digitized image data and an alpha-trimmed-mean smoothed version of said digitized image data to form corrected digital image values;

ii. determining a residuals distribution model for the corrected digital image values for step (i);

iii. determining a set of condition thresholds for a plurality of spatial contexts about a number of corrected digital image values to ensure a desired tolerable false alarm rate;

means for classifying each corrected image data value into an anomaly data value or a background data value as a function of said determined set of condition thresholds;

means for reclassifying to anomaly data values those background data values that are spatially near anomaly data values and whose corresponding corrected data values are less than but near to one or more of said determined set condition thresholds;

means for creating a list of the amount, size, location and shape of the identified anomalies by:

(a) segmenting the map of anomaly image values into contiguous regions;

(b) calculating for each region at least one of the following values: area, centroid location, bounding coordinates, eccentricity, and average density value; and (c) outputting a list of tabulated values.

10. A method for determining the presence of anomalies on the surface of a photographic element having a film grain, said film grain having an essentially Gaussian density distribution, said method comprising the steps of:

(a) forming non-enhanced original image data of a sample of the photographic element;

(b) storing the formed non-enhanced original image data produced from step (a);

(c) forming a smoothed rendition of the non-enhanced original image data, said smoothed rendition of the non-enhanced original image data effectively filtering said essentially Gaussian density distribution of said film grain and being resistant to the presence of said anomalies;

(d) conditioning the stored non-enhanced original image data to remove spatial variations not caused by anomalies by calculating the difference image between the non-enhanced original image data and the smoothed rendition of the non-enhanced original image data to form conditioned original image data values, said conditioned original image data values retaining said essentially Gaussian density distribution of said film grain; and (e) comparing the formed conditioned original image data values with a set of reference conditions to determine the existence of an anomaly, said reference conditions being determined by fitting a Gaussian probability distribution model to the conditioned original image data values and determining a plurality of thresholds which provide a desired tolerable number of background image data values being labeled as anomalies based upon the spatial context of a local region about each conditioned data value.

11. A method for determining the presence of anomalies on the surface of a photographic element having a film grain, said film grain having an essentially Gaussian density distribution, said method comprising the steps of:

(a) forming non-enhanced original image data of a sample of the photographic element;

(b) storing the formed non-enhanced original image data produced from step (a);

(c) forming a smoothed rendition of the non-enhanced original image data, said smoothed rendition of the non-enhanced original image data effectively filtering said essentially Gaussian density distribution of said film grain and being resistant to the presence of said anomalies;

(d) conditioning the stored non-enhanced original image data to remove spatial variations not caused by anomalies by calculating the difference image between the non-enhanced original image data and the smoothed rendition of the non-enhanced original image data to form conditioned original image data values, said conditioned original image data values retaining said essentially Gaussian density distribution of said film grain; and (e) comparing the formed conditioned original image data values with a set of reference conditions to determine the existence of an anomaly, said reference conditions being determined by analyzing Gaussian probability statistics of said film grain to produce a plurality of thresholds which provide a desired tolerable number of background image data values being labeled as anomalies based upon the spatial context of a local region about each conditioned data value.

12. A method for determining the presence of anomalies on the surface of a medium having a Gaussian density distribution, said method comprising the steps of:

(a) forming non-enhanced original image data of a sample of the medium;

(b) storing the formed non-enhanced original image data produced from step (a);

(c) forming a smoothed rendition of the non-enhanced original image data, said smoothed rendition of the non-enhanced original image data effectively filtering said essentially Gaussian density distribution of said medium and being resistant to the presence of said anomalies;

(d) conditioning the stored non-enhanced original image data to remove spatial variations not caused by anomalies by calculating the difference image between the non-enhanced original image data and the smoothed rendition of the non-enhanced original image data to form conditioned original image data values, said conditioned original image data values retaining said essentially Gaussian density distribution of said medium; and (e) comparing the formed conditioned original image data values with a plurality of reference conditions based on Gaussian probability statistics of said medium to determine the existence of an anomaly, said reference conditions being determined by fitting a Gaussian probability distribution model to the conditioned original image data values and determining a plurality of thresholds which provide a desired tolerable number of background image data values being labelled as anomalies based upon the spatial context of a local region about each conditioned data value.

* * * * *